US012594101B1

(12) United States Patent
 Piluiko

(10) Patent No.: US 12,594,101 B1
(45) Date of Patent: *\*Apr. 7, 2026

(54) METHOD AND DEVICE FOR BONE FIXATION

(71) Applicant: Vitaly Piluiko, Las Cruces, NM (US)

(72) Inventor: Vitaly Piluiko, Las Cruces, NM (US)

( * ) Notice: Subject to any disclaimer, the term of this patent is extended or adjusted under 35 U.S.C. 154(b) by 17 days.

This patent is subject to a terminal disclaimer.

(21) Appl. No.: 18/822,237

(22) Filed: Sep. 1, 2024

Related U.S. Application Data

(63) Continuation-in-part of application No. 17/676,126, filed on Feb. 19, 2022, now Pat. No. 12,076,066.

(60) Provisional application No. 63/151,791, filed on Feb. 21, 2021.

(51) Int. Cl.
| *A61B 17/80* | (2006.01) |
| *A61B 17/88* | (2006.01) |
| *A61B 17/56* | (2006.01) |

(52) U.S. Cl.
CPC ........... *A61B 17/808* (2013.01); *A61B 17/88* (2013.01); *A61B 2017/564* (2013.01)

(58) Field of Classification Search
CPC ... A61B 17/56; A61B 2017/564; A61B 17/80; A61B 17/8004; A61B 17/8019; A61B 17/808; A61B 17/88; A61B 17/8866; A61B 17/8872
See application file for complete search history.

(56) References Cited

U.S. PATENT DOCUMENTS 5,951,557 A * 9/1999 Luter ..................... A61B 17/80
606/71
12,076,066 B1 * 9/2024 Piluiko .............. A61B 17/8866

* cited by examiner

*Primary Examiner* — Larry E Waggle, Jr.
(74) *Attorney, Agent, or Firm* — Fred Zollinger

(57) ABSTRACT

A method and device for repairing a bone fracture include the use of a bone plate and a bone hook that engages the interior of the bone. The method includes the steps of using at least one bone hook that engages the interior of the bone to apply a counterforce to the bone plate installation forces.

18 Claims, 12 Drawing Sheets

METHOD AND DEVICE FOR BONE FIXATION

CROSS REFERENCE TO RELATED APPLICATIONS

This application is a continuation-in-part application claiming priority to U.S. patent application Ser. No. 17/676, 126 filed Feb. 19, 2022, which application claims the benefit of U.S. Provisional Patent Application No. 63/151,791 filed Feb. 21, 2021; the disclosures of each are incorporated herein by reference.

BACKGROUND OF THE DISCLOSURE

1. Technical Field

The disclosure relates to bone plates and methods for installing bone plates. More particularly, the disclosure relates to the use of at least one bone hook or anchor that engages the interior of the bone to position and hold the bone while a bone plate is attached to the bone. Specifically, the disclosure provides an exemplary configuration wherein two bone hooks or anchors engage interior portions of the fractured bone to position the bone and then apply a counterforce during the installation of the bone screws. In this configuration, the bone hooks are positioned in a slot defined by the bone plate.

2. Background Information

Chest traumas, in particular rib fractures, are common. These fractures comprise about twelve percent of all fractures in patients, particularly the elderly. The most common complication of rib fractures is pneumonia which may be fatal. This is largely due to pain and splinting effects, preventing effective coughs and breathing. Treatment includes operative and non-operative methods. Pain medications and sometimes mechanical ventilation used in non-operative treatment may have major side effects. Non-operative treatment is associated with a prolonged stay in the hospital and possibly prolonged use of narcotic medications. Operative treatment is attractive as it may reduce long-term pain by immobilizing the broken edges of the bone and thus reducing pain. It involves alignment and stabilization of the rib fractures by using internal fixation devices or bone plates. Bone plates are stiff devices (usually metal such as titanium) positioned on the surface of the bone crossing the location of the fracture. The plate is connected to the bone with fasteners such as screws. A significant reduction in pneumonia rates has been found in surgically treated patients, 90% vs 22% at 21 days after surgery.

Although the use of bone plates is associated with desirable outcomes, the anatomy of the chest wall presents limitations to the use of the bone plates for several reasons. First, the underlying fine lining of the pleura can be easily violated with instrumentation leading to pneumothorax, potentially a life threatening condition. Second, between the ribs there is an intercostal space where the intercostal artery and nerve are found. Injury to these structures can occur leading to bleeding and excessive pain. Third, ribs are very soft bone and can bow away from the tools under the pressure of the drilling and screwing during the installation of the bone plate. Also, the procedure commonly requires holding the rib and plate with clamps. When clamps are used that engage the sides of the ribs, the intercostal structures are violated. In order to apply these clamps, the incision of the chest wall has to be extended. Exposure of the rib/rib fractures may lead to a large incision which is an additional source of pain due to the incision size. Therefore, a minimally invasive approach that allows reliable reduction of the rib fracture and subsequent firm immobilization of the edges of the rib preventing even minimal movement may be ideal treatment of these injuries.

SUMMARY OF THE DISCLOSURE

The disclosure provides a methods, devices, and kits used to practice the methods. One exemplary method includes the steps of using at least one bone hook that engages the interior of the bone to apply a counterforce to the bone plate installation forces. The bone plate is configured to be positioned while the bone hook is in place. In an exemplary configuration, two bone hooks are used to position and then hold the ends of the fractured bone. The bone plate is positioned about the bone hooks and positioned over the bone ends. The bone hooks are used to apply a counterforce that is in opposition to the forces required to install the fasteners that secure the bone plate to the bone. The bone hooks are removed after the bone plate is installed. In the case of a rib fracture, with the hook or hooks engaging the interior of the bone, there is minimal damage to the intercostal material around the fracture and no engagement between the tools and the pleura behind the bone. With the bone hooks passing through the center of the bone plate, the size of the incision is minimized.

The disclosure provides different configurations for the bone hooks. One configuration provides a hook end extending away from a shank that is optionally connected to a handle. Another configuration is provided where the hook end is extendable and retractable with respect to the shank. In this configuration, the hook end is selectively pushed out of the end of the shank when it is to engage the bone and is retracted when the bone hook is to be removed. A biased plunger is optionally used to control the movement of the hook end. A further configuration provides the hook ed with a thread and the hook end connected to a handle that allows the user to rotate the hook end. This configuration can be combined with the extendable and retractable configuration.

In one configuration, the disclosure provides a bone plate that has a body that can be flat or curved to match the curvature of the bone on which it is to be used. The body has a central portion located between a first end portion and a second end portion. Each of the end portions defines at least one fastener hole. The central portion defines an elongated slot. The slot has a width and a length. In combination with the bone plate, first and second bone hooks are provided to define a bone plate installation kit. Each bone hook has a shank and a hook. In use, the shanks of the bone hooks are located in the slot of the bone plate. Each shank has a maximum cross sectional dimension (such as a diameter or a width) that is smaller than the width of the slot which allows the user to manipulate the bone hooks when they are through the plate.

In another configuration, the disclosure provides a bone plate that has a body that can be flat or curved to match the curvature of the bone on which it is to be used. The body has a central portion located between a first end portion and a second end portion. Each of the end portions defines at least one fastener hole. The central portion defines an elongated slot that is open to an edge of the body at a neck. The slot has a width and a length. The neck has a minimum width. In combination with the bone plate, first and second bone hooks are provided to define a bone plate installation kit. Each bone hook has a shank and a hook. In use, the shanks of the bone hooks are located in the slot of the bone plate. Each shank has a maximum cross-sectional dimension (such as a diameter or a width) that is smaller than the width of the slot and smaller than the minimum width of the neck. This allows the bone plate to be moved onto the bone hooks by passing the bone hook shanks through the neck.

The disclosure provides a configuration that uses collapsible and expandable bone anchors that are placed with a device that can also function as a bone hook. The anchors are collapsed and placed in a hollow end of a bone hook. The end of the bone hook is located inside a bone through the fractured end. The user then pushes the collapsed anchor out of the hollow end where it expands and engages the interior of the bone. A suture is connected to the anchor which allows the user to manipulate the bone by pulling on the suture. After two anchors are installed in opposite sides of a fractured bone, the fractured ends are positioned and then the sutures are joined by tying or with a crimping tool. This arrangement is then used to provide a counterforce during the installation of the bone plate.

The individual features may be combined in different combinations than specifically described below to form different configurations of the device of the disclosure. The preceding non-limiting aspects of the disclosure, as well as others, are more particularly described below. A more complete understanding of the devices, assemblies, and methods can be obtained by reference to the accompanying drawings, which are not intended to indicate relative size and dimensions of the assemblies. In those drawings and the description below, like numeric designations refer to components of like function. Specific terms used in that description are intended to refer only to the particular structure of the embodiments selected for illustration in the drawings, and are not intended to define or limit the scope of the disclosure.

4

Figure 15:
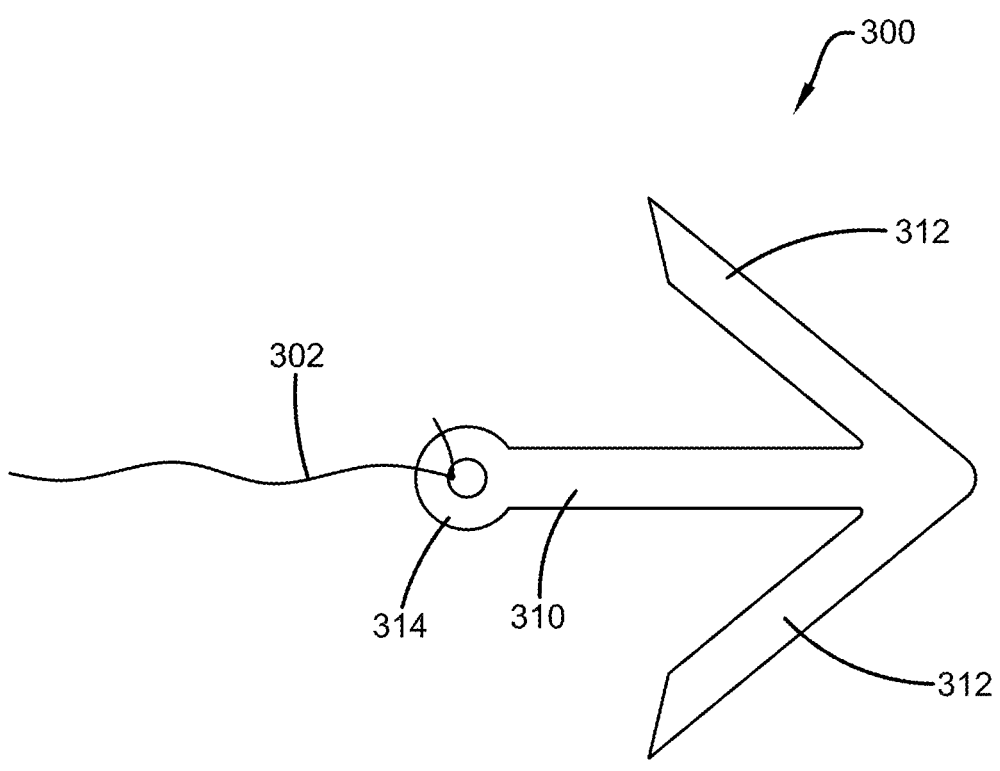

FIG. 15 is a view of a bone anchor in its expanded condition.

Figure 16:
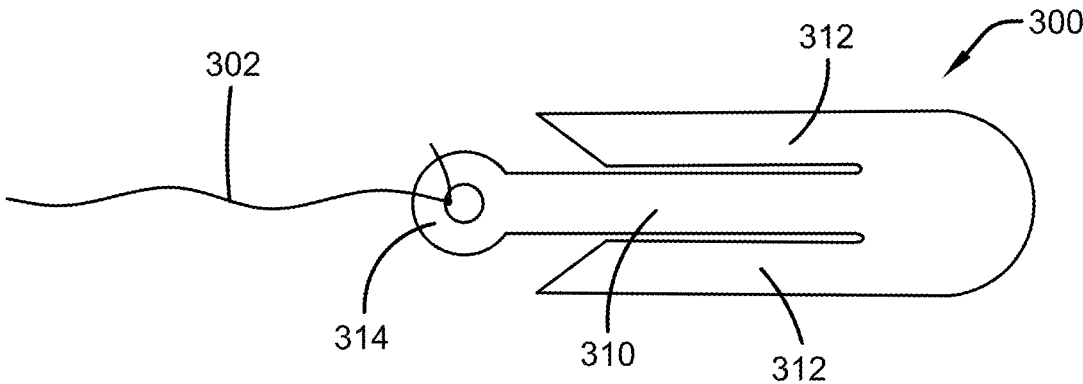

FIG. 16 is a view of the bone anchor of FIG. 15 in its collapsed condition.

Figure 17:
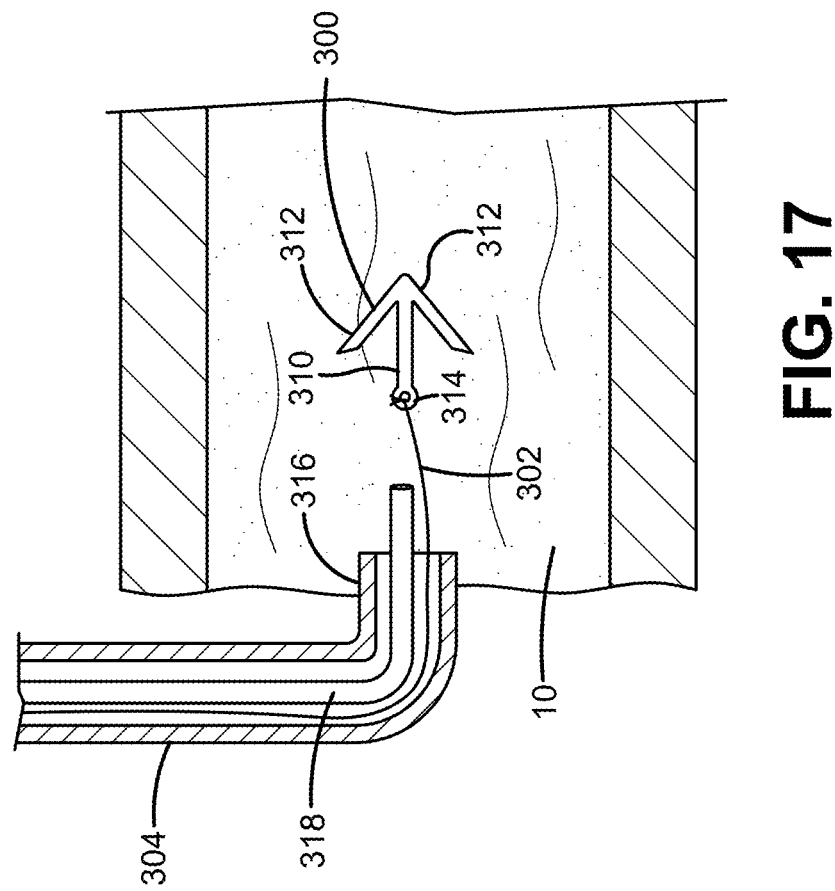

FIG. 17 is a view of the bone anchor being installed in the fractured end of a bone.

Figure 18:
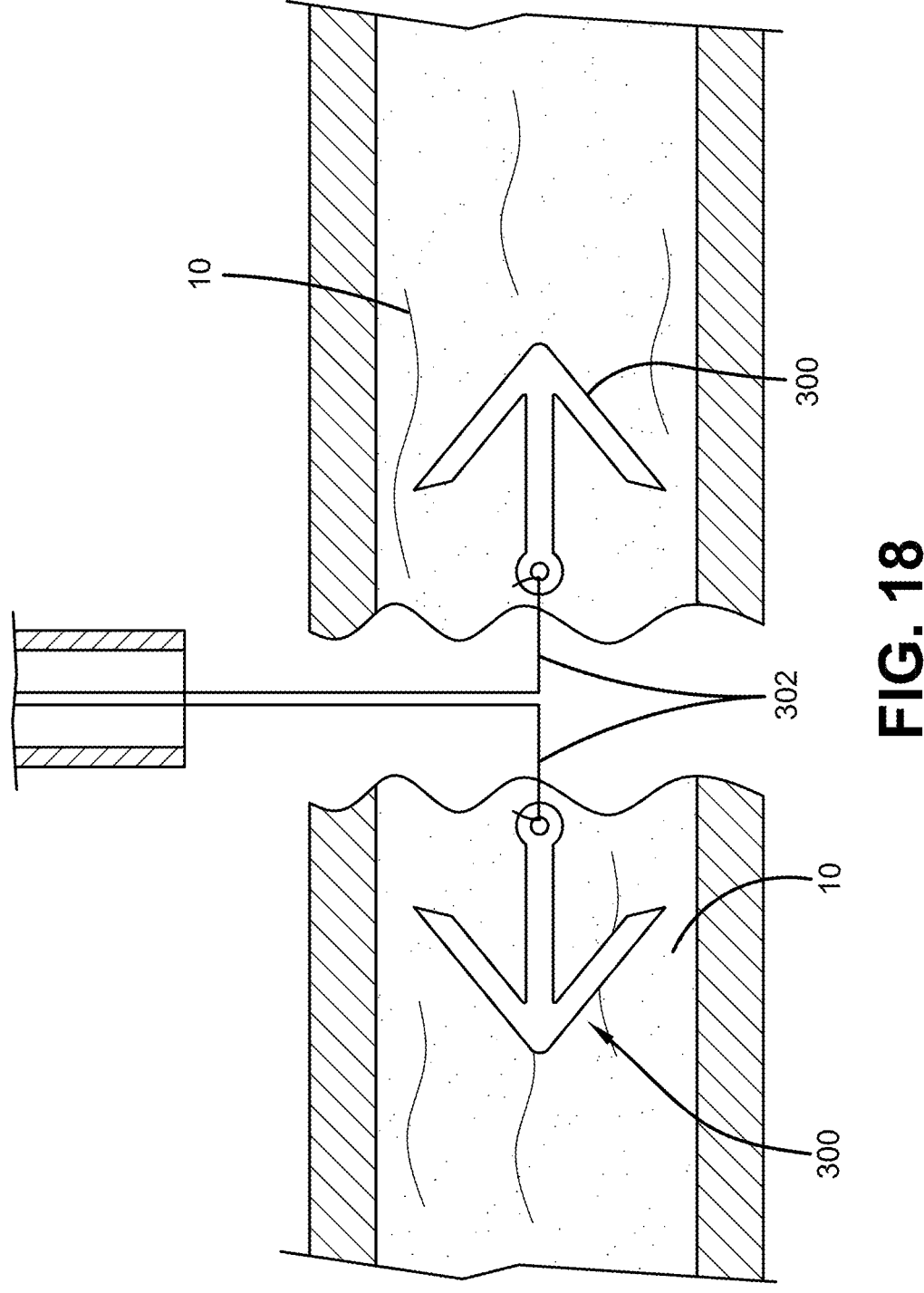

FIG. 18 is a view showing two bone anchors installed in the two ends of a fractured bone with the sutures extending out of the bone ends.

DETAILED DESCRIPTION OF THE DISCLOSURE

The disclosure provides an exemplary method, a device in the form of a bone plate 2, and a kit 4 used to practice the method. Kit 4 includes the combination of bone plate 2 and first and second bone hooks 6 that cooperate with bone plate 2. The method includes the steps of using at least one bone hook 6 to engage the interior of a fractured bone 10 to apply a counterforce to the bone plate installation forces. The bone hook 6 passes through the bone plate 2. In general, the method minimizes the size the incision required to operate on a bone fracture and the disruption to the material around the fracture is minimized. In the case of a rib fracture, with hooks 6 engaging the interior of bone 10, there is minimal damage to the intercostal material 12 around the fracture and no engagement between the tools and the pleura 14 behind bone 10.

Figures 1, 2, 3, 4, 5:
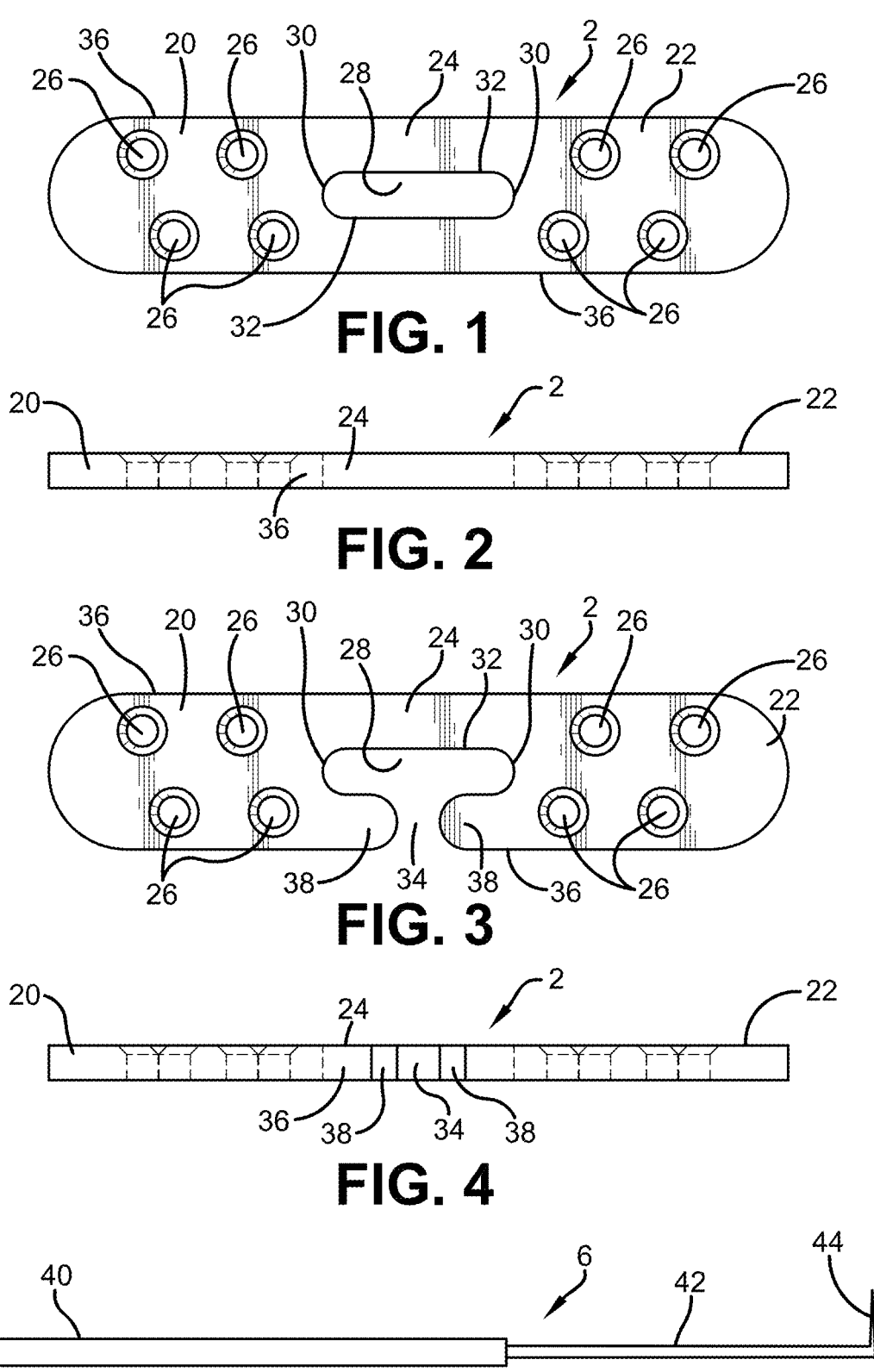
FIG. 1 is a top plan view of a first exemplary embodiment of the bone plate of the disclosure.
FIG. 2 is a front view of FIG. 1.
FIG. 3 is a top plan view of a second exemplary embodiment of the bone plate of the disclosure.
FIG. 4 is a front view of FIG. 3.
FIG. 5 is a side view of a bone hook that is used with the bone plate of the disclosure.
Figure 6:
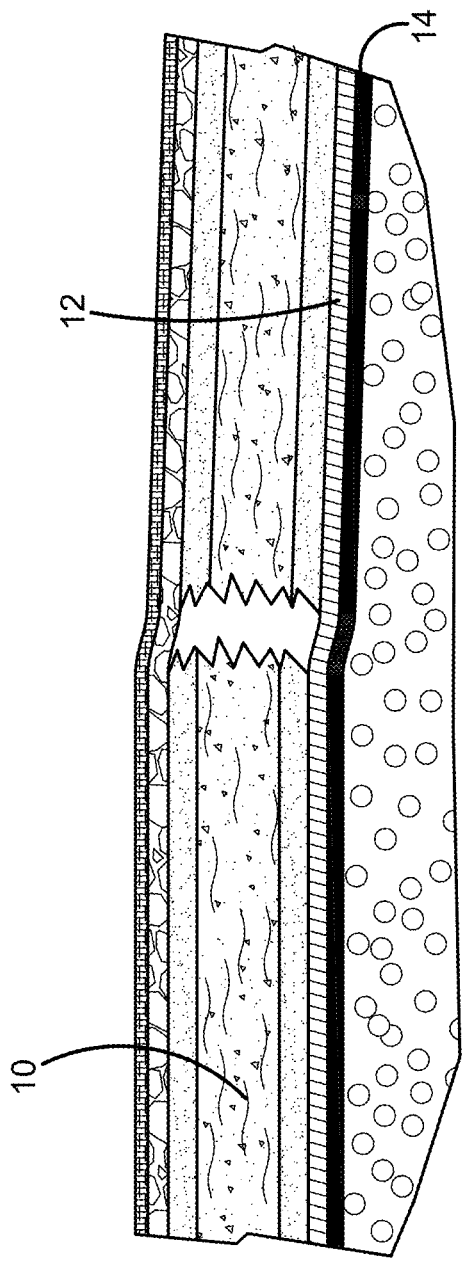
FIG. 6 is a section view of an exemplary bone fracture.
Figure 7:
FIG. 7 is a view similar to FIG. 6 with a first bone hook inserted into a first bone end.
Figure 8:
FIG. 8 is a view similar to FIG. 6 with a second bone hook inserted into a second bone end.
Figure 9:
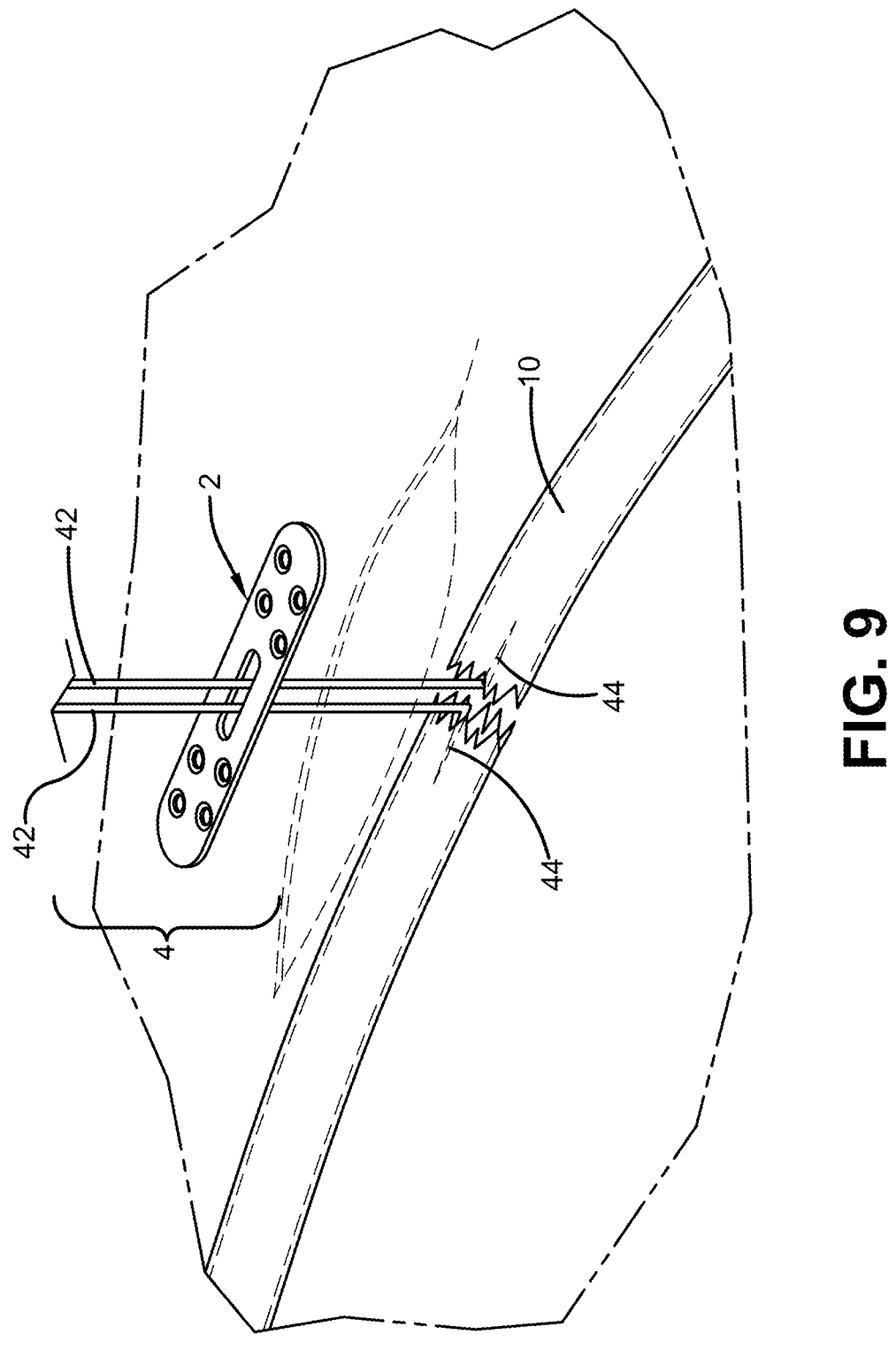
FIG. 9 is a perspective view showing how the bone ends have been repositioned with the bone hooks and a bone plate positioned over the bone hooks.
Figure 10:
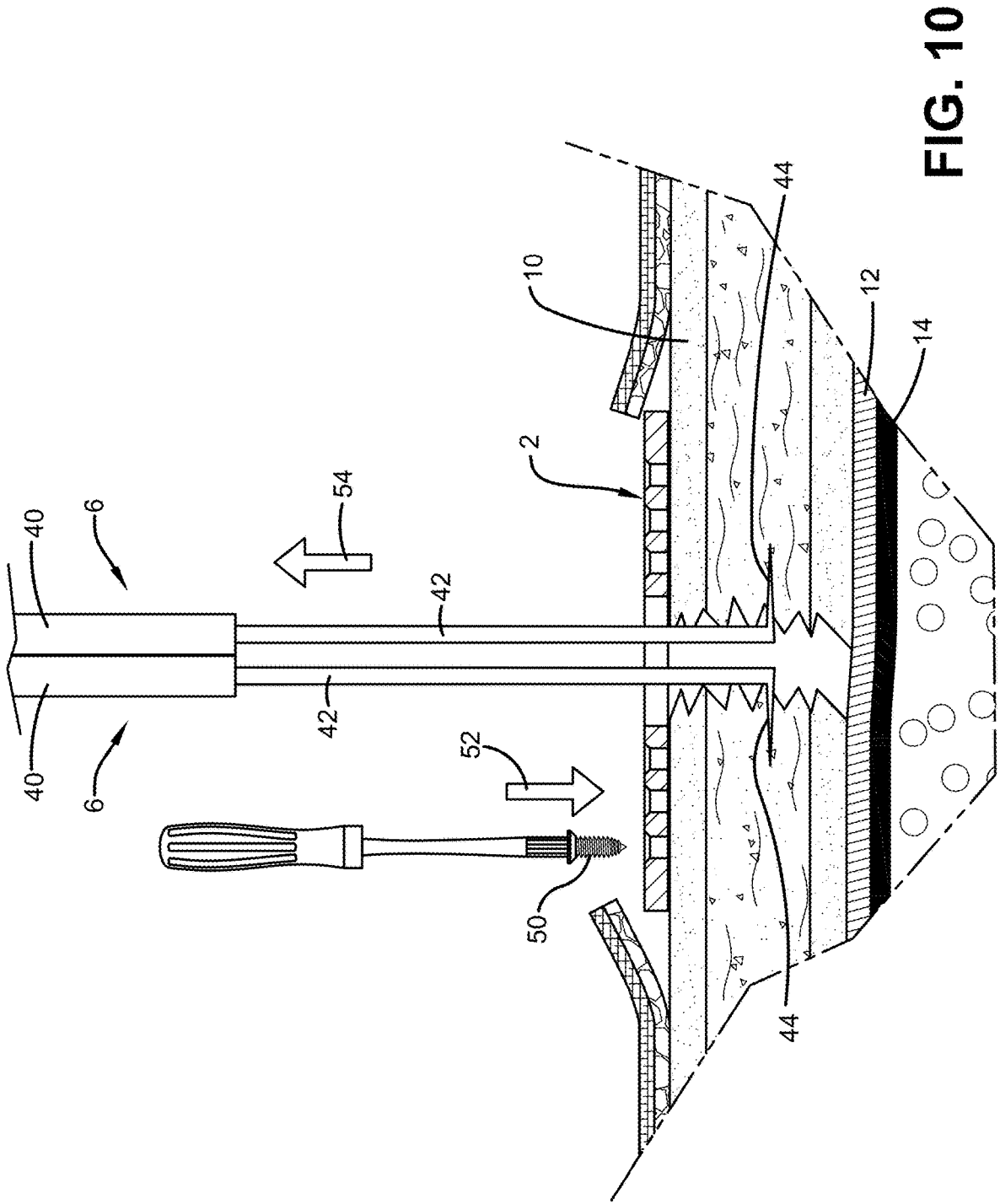
FIG. 10 is a view similar to FIG. 6 showing a counterforce being applied by the bone hooks while a first bone screw is installed.
Figure 11:
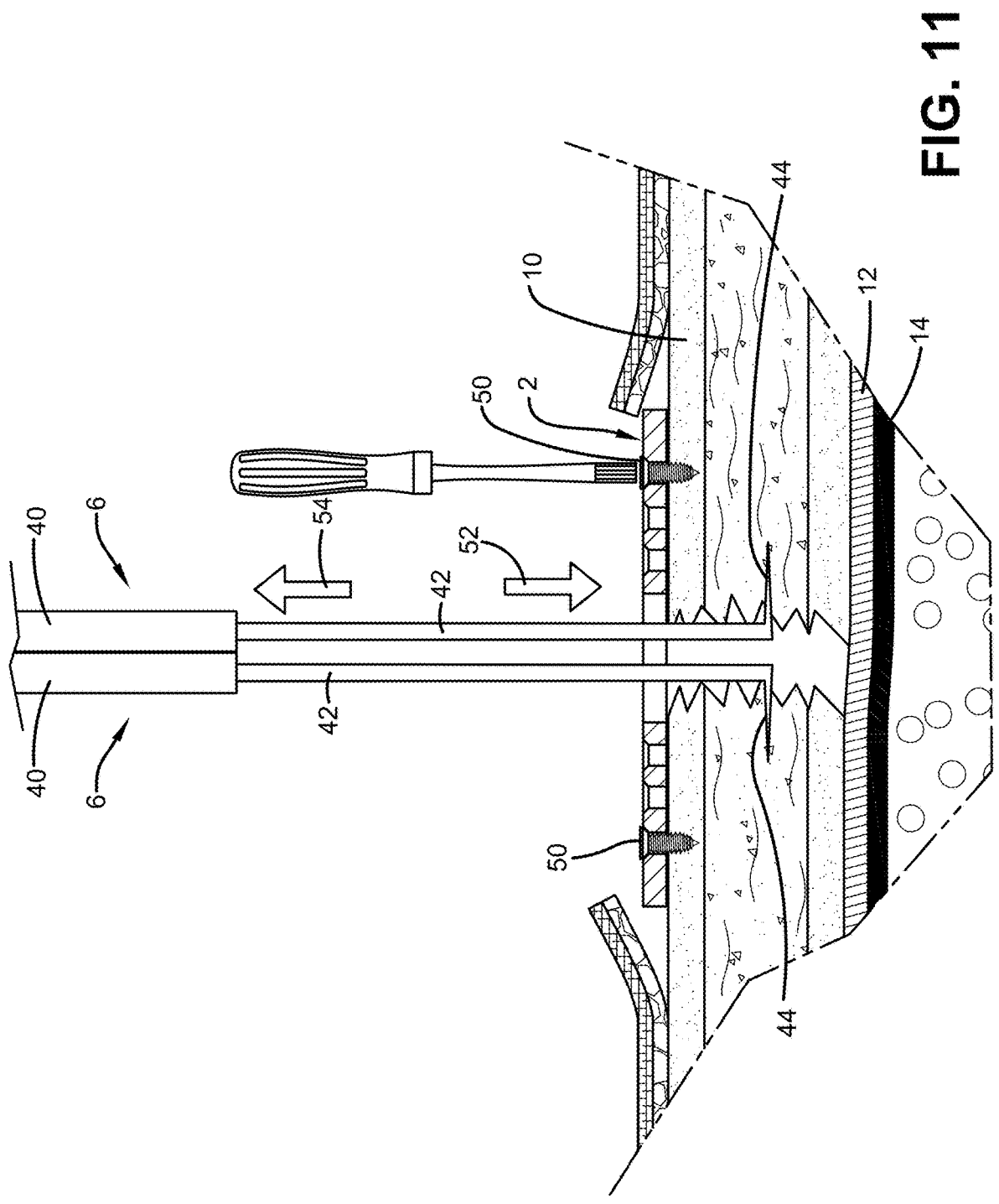
FIG. 11 is a view similar to FIG. 6 showing a counterforce being applied by the bone hooks while a second bone screw is installed.
Figure 12:
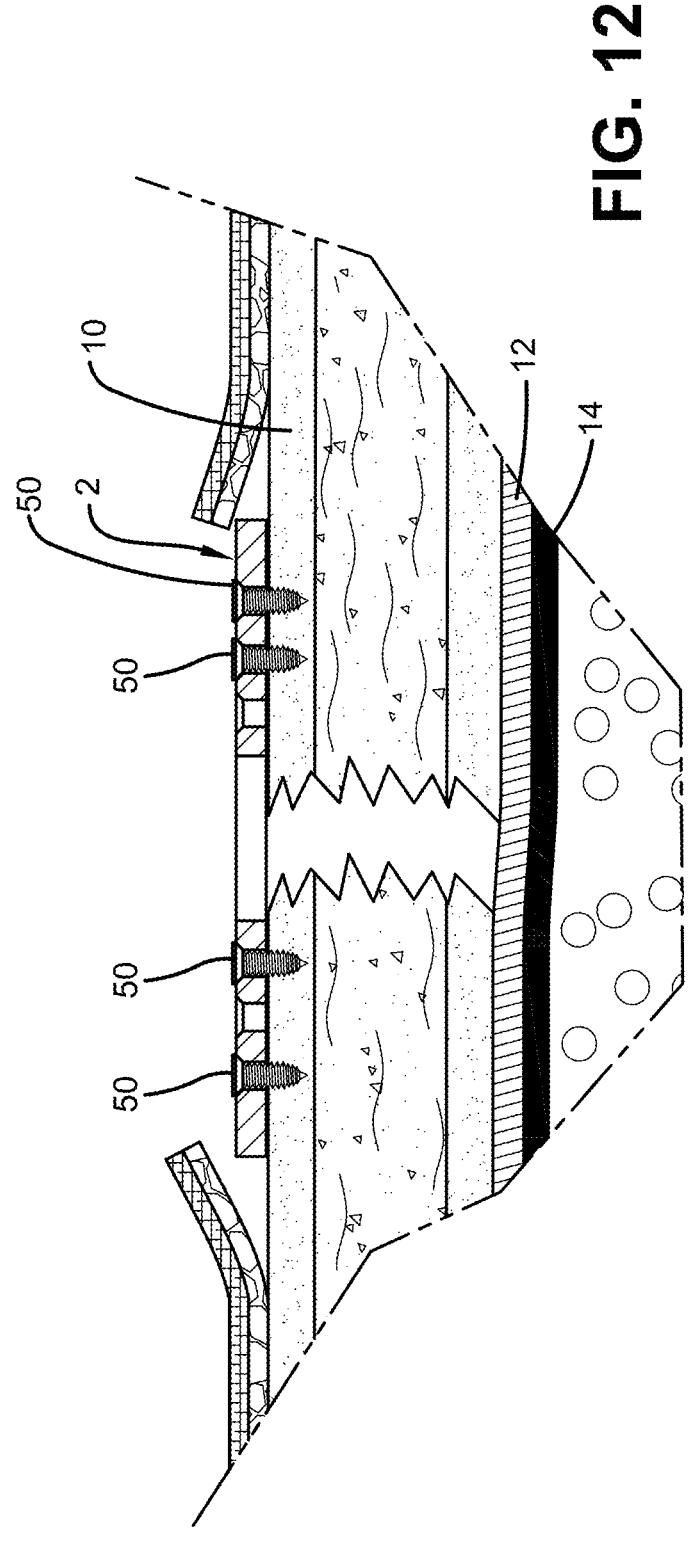
FIG. 12 is a view similar to FIG. 6 showing the bone plate installed and the bone hooks removed.

A first exemplary configuration of bone plate 2 is depicted in FIGS. 1 and 2. Although the exemplary configuration is depicted as being a flat plate, bone plate 2 can be curved about one or more of its axes to complement the shape of bone 10 with which it will be used. Bone plate 2 can be made from a biocompatible material such as stainless steel, cobalt base alloys, bioceramics, titanium alloys, pure titanium, composite materials, and polymers. Although the size and shape of the body of bone plate 2 varies for use with different bones, each body includes a first end portion 20, a second end portion 22, and a central portion 24. Each end portion 20 and 22 defines at least one fastener opening 26 that is configured to receive a fastener, such as a bone screw, that secures bone plate 2 to bone 10. In the exemplary configuration, fastener openings 26 are round openings. Each end portion 20 and 22 defines four fastener openings 26. In each end portion 20 and 22, fastener openings 26 are spaced from their edges the same distances such that two sets of two fastener openings 26 are aligned in the longitudinal direction of bone plate 2 in each end portion 20 and 22. Fastener openings 26 are offset from each other across the centerline of bone plate 2. Central portion 24 defines a slot 28 that is sized to loosely accommodate both bone hooks 6 at the same time. Slot 28 is elongated in the longitudinal direction of bone plate and can be centered with respect to the length and width of the body of bone plate 2. The ends 30 of slot are semi-circular. The walls 32 that define the sides of slot 28 are straight. Slot 28 has a width between walls 32 and a length between ends 30. In the exemplary configurations, the length is four times the width but in other configurations, the length of slot 28 can be two to eight times the width. In the second exemplary configuration, the body of bone plate 2 defines an open neck 34 that connects slot 28 with an edge 36. Neck 34 has a minimum opening between the two shoulders 38 that define neck 34. The ends of shoulders 38 are rounded. The minimum opening dimension can be the same as the width of slot 28 or slightly larger than the maximum dimension of the portion of bone hook 6 that is moved through neck 34 during the method.

Each bone hook 6 includes a handle 40, a shank 42, and a hook end 44. Handle 40 is optional. Shank 42 is a thin compared with the width of slot 28 and has a length sufficient to allow the user to place hook end 44 into fractured bone 10. Hook end 44 is tapered to a sharp point. Handle 40 and shank 42 are sized to fit through slot 28. The maximum lateral cross sectional dimension (such as a width or diameter) of handle 40 and shank 42 is smaller than the width of slot 28. Shank 42 is sized such that two shanks 42 can be located in slot 28 at the same time and moved around within slot 28. Bone plate 2 can thus be moved down over handle 40 and shank 42 or bone plate 2 can be moved onto shank 42 by passing shank 42 through neck 34. In the exemplary configuration, the maximum cross section shank dimension is about a third of the width of slot 28. In other configurations, the shank dimension is a tenth to two-thirds of the width of slot 28.

After surgical access and limited bone 10 exposure, hook ends 44 are placed in the bone marrow of both ends of the broken bone 10. The surgeon reduces the fracture by moving both ends of the broken bone 10 in opposing and aligned positions. As an option, temporary holding screws are drilled closely to the broken ends of the bone 10. As an option, hooks 6 and screws can be placed prior to the application of the hooks through the plate slot 28 first. With the ends of the bone 10 aligned, bone plate 2 is placed over bone hooks 6 with bone hooks 6 located in slot 28. In the second configuration, bone plate 2 is moved onto shanks 42 by passing shanks 42 through neck 34. Bone plate 2 is lowered over the bone 10. Bone plate 2 can be held in position with shanks 42. Using the bone hooks 6 (and optionally temporary screws) for holding the bone 10 in the aligned position, fasteners 50 such as fixating screws are placed through openings 26 into bone 10. The force 52 necessary for installing fasteners 50 down or inwardly is countered by the opposing force 54 holding bone hooks 6 (or optionally holding temporary screws) as they are pulled up. After fasteners 50 are installed, bone hooks 6 are removed.

The following are advantages of this method and use of this plate for rib fracture reduction and fixation:

It accomplishes bone fixation with a minimal incision that only provides access to the area of the fracture.

It allows visual realignment of the fractured segments of the rib 10 utilizing bone hooks 6.

It provides a counterforce 54 for application of the screws 50.

It provides an elongated slot 28 for placing the bone hooks 6.

The neck opening 34 in the bone plate 2 provides access to slot 28 for ease of applying the bone plate 2 around the bone hooks 6.

There is elimination of the need for applying clamps on the bone 10 and the bone plate 2 to affix them for drilling the screws 50.

It avoids opening the intercostal space and the pleural space with less trauma to the soft tissue.

The bone plate 2 is applied with the help of the bone hooks 6 or in combination with the bone hooks 6 and the holding drill for temporary bone suspension and as counterbalance for drilling the screws 50 into the bone 10.

Figures 13, 14:
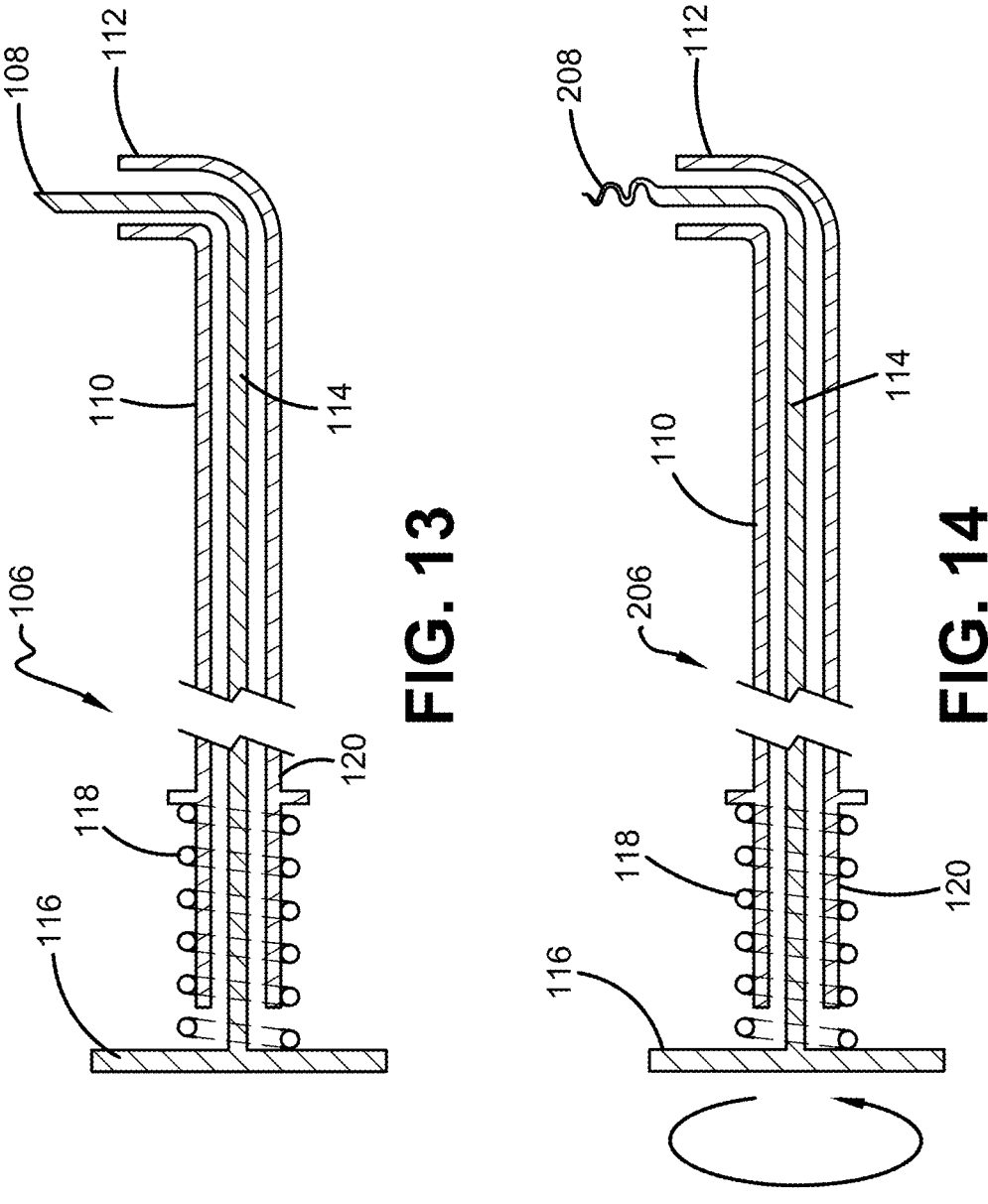
FIG. 13 is a section view showing an alternative configuration of a bone hook.
FIG. 14 is a section view showing another alternative configuration of a bone hook.

A first alternative embodiment of a bone hook is indicated generally by the number 106 in FIG. 13. Bone hook 106 includes an extendable and retractable hook end 108. When hook end 108 is in its extended position or condition, bone hook 106 functions similar to bone hook 6 described above. When hook end 108 is in its retracted position or condition, bone hook 106 has a smaller profile and is easier to position in a fracture and easier to remove from the fracture.

In the exemplary configuration depicted in FIG. 13, bone hook 106 includes a hollow shank 110 having a curved tip 112. Hook end 108 is either integral with or connected to a flexible shaft 114 that is connected to a plunger 116. Non-limiting examples of flexible shaft 114 include a length of wire, a piece of thin metal or polymer, and a plurality of linked sections of material. Each is flexible enough to retract into curved tip 112 while also being able to provide a counter holding force during the installation of the bone plate. Shaft 114 can be solid or hollow. Plunger 116 can be biased towards its retracted position with a biasing member 118 such as the spring depicted in the drawings. Biasing member 118 is either located outside of a handle 120 or on the inside of handle 120. Biasing member 118 biases plunger 116 outwardly to retract hook end 108. Optionally, a stop is used to limit the movement of shaft 114 with respect to shank 110 and handle 120. Optionally, a latch is used to hold plunger in the extended position to allow bone hook 106 to be used in the same manner as bone hook 6 described above.

After positioning curved tip 112 into the area of the fracture and then further inside of the bone marrow of one of the broken bone edges, the surgeon applies pressure on plunger 116 to advance hook end 108 into the bone marrow. The surgeon can then latch plunger 116 in place to maintain hook end 108 in the extended condition while bone hook 106 is used to help secure a bone plate. When bone hook 106 is no longer needed, plunger 116 is unlatched and hook end 108 is retracted. This makes the profile of bone hook 106 smaller to make it easier to remove it from the patient.

In the exemplary configuration depicted in FIG. 14, bone hook 206 includes some of the same features as bone hook 106 and the same numbers are used to refer to these features. This configuration of bone hook 206 is used in a manner similar to bone hook 106 with respect to the extension and retraction of hook end 208. In this configuration, hook end 108 is in the form of a thread, a screw tip, a corkscrew, or a pig tail. Plunger 116 can be rotated to screw hook end 208 into the bone marrow or bone material. Plunger 116 is made with option of rotation both when it is being pushed down and when resting to rotate shaft 114 and hook end 208. A surgeon by applying pressure and rotational movement on plunger 116, advances hook end 208 like an advancing screw into the bone marrow. After the plate is placed, counterrotation of the plunger 116 unscrews hook end 208 out of the bone marrow to where it retracts into curving tip 112 which helps the removal of hook 206.

With both bone hook embodiments of FIGS. 13 and 14, two hooks are installed into the opposite ends of the fracture. Once hook ends are in the bone marrow on both sides of the fracture, traction is applied to vertically align the broken bone segments. A bone plate is fashioned around both hooks through its slot, then lowered down on the bone and secured with screws. After the plate is secured, the surgeon or surgeon's assistant releases the pressure on plunger 116 (or releases the latch) and both hook ends are retracted into the curving tips 112. The hooks are then removed.

An alternative embodiment of the method, device, and kit of the disclosure is described with reference to FIGS. 15-18. In this embodiment, self-expanding bone anchors 300 are installed in the ends of the fracture. Sutures 302 connected to the anchors allow the user to exert force on the bone end through anchors 300.

In this embodiment, a hollow cylinder 304 similar to bone hooks 106 and 206 is loaded with a self-expanding, collapsible bone anchor 300. Anchor 300 has a bar 310 and attached foldable needles 312. At the base of bar 310 there is an opening 314 that used for attaching suture 302.

Needles 312 can be folded toward bar 310 and loaded into the tip 316 of the hollow cylinder 304. A movable shaft 318 connected to a plunger (similar to that described above) can be used to advance anchor 300 out of the hollow cylinder into bone marrow 10. Once anchor 300 is out of the cylinder, needles 312 spring out to an expanded condition with respect to bar 310. By gentle pulling on suture 302, the surgeon makes sure that anchor 300 is firmly attached to the inside of the bone. The same maneuver is performed on the other segment or segments of broken bone. Both sutures 302 brought outside of the fractured area and then tied, crimped, or fastened together with a tool such as that sold under the COR-KNOT registered trademark owned by LSI Solutions, Inc. Such a device can be used to secure both sutures 302 together. Tension on the sutures 302 brings both ends of the bone together. The joined sutures 302 are then used in the same fashion as the hooks to stabilize the bone for application of the plate.

Placement of the anchors 300 can be done without a formal incision. The surgeon creates a small stab wound on the skin, advance the instruments through the stab wound, subcutaneous tissue and muscle layers directly into broken bone area under Xray or thoracoscopy guidance. Anchor devices 300 can be used for placement of the plate or used alone by simply immobilizing the edges of the bone with joining the sutures 302 together.

In the foregoing description, certain terms have been used for brevity, clearness, and understanding. No unnecessary limitations are to be implied therefrom beyond the requirement of the prior art because such terms are used for descriptive purposes and are intended to be broadly construed. Moreover, the above description and attached illustrations are an example and the invention is not limited to the exact details shown or described. Throughout the description and claims of this specification the words "comprise" and "include" as well as variations of those words, such as "comprises," "includes," "comprising," and "including" are not intended to exclude additives, components, integers, or steps.

The invention claimed is:

1. A bone plate installation kit comprising:
a bone plate and first and second bone hooks;
the bone plate having a central portion located between a first end portion and a second end portion;
each of the end portions defining at least one fastener opening;
the central portion defining an elongated slot having a length between slot ends and a minimum width;
each bone hook having a shank and a hook end; the shank of each bone hook being sized to allow both shanks to be located in and move around in the elongated slot at the same time and move independently of the other to point the hook ends in substantially opposite directions; and
each shank having a maximum width dimension that is no greater than two-thirds of the minimum width of the elongated slot.

2. The kit of claim 1, wherein the elongated slot has a length that is at least two times and at most eight times the minimum width of the elongated slot.

3. The kit of claim 1, wherein the elongated slot has a length that is greater than three times a diameter of the fastener opening in one of the end portions.

4. The kit of claim 1, wherein the plate defines a plurality of fastener openings in each end portion.

5. The kit of claim 1, wherein the hook end of at least one of the bone hooks is selectively extendable to an extended condition and selectively retractable to a retracted condition.

6. The kit of claim 5, wherein the selectively extendable and selectively retractable hook end is biased toward the retracted condition.

7. The kit of claim 5, wherein the shank of the at least one of the bone hooks has a curved tip through which the hook end extends and into which the hook end retracts.

8. The kit of claim 5, wherein the hook end is connected to a plunger.

9. The kit of claim 5, further comprising a latch that holds the hook end in the extended condition.

10. The kit of claim 5, wherein the hook end is rotatable with respect to the shank; the hooks end having a portion in the form of one of a thread, a screw tip, a corkscrew, and a pig tail.

11. The kit of claim 10, further comprising a plunger that selectively rotates the hook end.

12. A method of installing a bone plate over a bone fracture comprising the steps of:
positioning a first bone hook through a slot in a bone plate; the bone hook having a shank and a hook end;
moving the hook end into an interior of one bone end on one side of a fractured bone through a fractured end of the fractured bone; and
supporting the one bone end on one side of the fracture of a fractured bone with the first bone hook by providing an outward counterforce working against an inward force created during installation of a bone fastener into the one bone end through the bone plate.

13. The method of claim 12, further comprising the step of extending the hook end from a retracted position to an extended position with respect to the shank.

14. The method of claim 13, further comprising the step of rotating the hook end to screw it into the interior of the one bone end.

15. The method of claim 13, wherein the shank has a curved tip and the hook end is connected to a plunger with a shaft; the method further comprising the step of bending at least a portion of the hook end and shaft through the curved tip as the hook end is moved from the retracted position to the extended position.

16. A method of installing a bone plate over a bone fracture comprising the steps of:
inserting a first self-expanding bone anchor into an interior of one bone end on one side of a fractured bone through a fractured end of the fractured bone;
inserting a second self-expanding bone anchor into an interior of the other bone end on the other side of the fractured bone through the other fractured end of the fractured bone;
connecting the first and second self-expanding bone anchors together with a connector; and
moving the bone ends together with force on the connector.

17. The method of claim 16, further comprising the step of supporting the one bone end by providing an outward counterforce on the connector that works against an inward force created during installation of a bone fastener into one of the bone ends through a bone plate.

18. The method of claim 16, wherein each of the self-expanding bone anchors is inserted into the bone end in a collapsed condition and allowed to self expand to an expanded condition.

* * * * *